(12) United States Patent
Furusato et al.

(10) Patent No.: US 7,304,723 B2
(45) Date of Patent: Dec. 4, 2007

(54) LIGHT SOURCE UNIT, PHOTORECEPTIVE UNIT AND MULTICHANNEL PHOTODETECTOR USING THE SAME

(75) Inventors: Noriaki Furusato, Kyoto (JP); Atsushi Murakami, Kyoto (JP)

(73) Assignee: Arkray, Inc., Kyoto (JP)

( * ) Notice: Subject to any disclaimer, the term of this patent is extended or adjusted under 35 U.S.C. 154(b) by 340 days.

(21) Appl. No.: 10/532,795

(22) PCT Filed: Oct. 23, 2003

(86) PCT No.: PCT/JP03/13517

§ 371 (c)(1),
(2), (4) Date: Apr. 25, 2005

(87) PCT Pub. No.: WO2004/038350

PCT Pub. Date: May 6, 2004

(65) Prior Publication Data

US 2006/0102828 A1 May 18, 2006

(30) Foreign Application Priority Data

Oct. 25, 2002 (JP) .............................. 2002-311726

(51) Int. Cl.
*G01N 21/64* (2006.01)
(52) U.S. Cl. ...................................................... 356/73
(58) Field of Classification Search ...................... None
See application file for complete search history.

(56) References Cited

U.S. PATENT DOCUMENTS 4,284,412 A    8/1981   Hansen et al.

2002/0043636 A1*  4/2002  Kimura ..................... 250/585
2003/0048539 A1*  3/2003  Oostman et al. ............ 359/634

FOREIGN PATENT DOCUMENTS

| JP | 62-245942   | 10/1987 |
| JP | 11-101691   | 4/1999  |
| JP | 2001-117013 | 4/2001  |
| JP | 2002-515602 | 5/2002  |
| WO | WO 99/60380 | 11/1999 |

* cited by examiner

*Primary Examiner*—Tu T Nguyen
(74) *Attorney, Agent, or Firm*—Hamre, Schumann, Mueller & Larson, P.C.

(57) ABSTRACT

A reaction container, a light source unit including light emitting devices that are different in wavelength of an emitted light beam and output dichroic mirrors that are different in wavelength range of a reflectible light beam, and a photoreceptive unit including photoreceptors and photoreceptive dichroic mirrors that are different in wavelength range of a reflectible light beam are used. The light emitting devices are arranged so that output directions thereof may be in parallel, and the output dichroic mirrors are arranged so that the reflected light beams may pass through the same optical path in the same direction. The photoreceptors are arranged so that photoreceptive surfaces may be in parallel, and the photoreceptive dichroic mirrors are arranged so that output light beams from the reaction container may be reflected by the photoreceptive dichroic mirrors and may enter the photoreceptors, according to wavelengths of the output light beams.

3 Claims, 5 Drawing Sheets

US 7,304,723 B2

LIGHT SOURCE UNIT, PHOTORECEPTIVE UNIT AND MULTICHANNEL PHOTODETECTOR USING THE SAME

TECHNICAL FIELD

The present invention relates to a light source unit, a photoreceptive unit and a multichannel photodetector using the light source unit and the photoreceptive unit, and more specifically, relates to a multichannel photodetector used in, for example, genetic diagnoses.

BACKGROUND ART

Recently, due to the development of genetic analytical techniques, the use of genetic diagnoses for diagnosing the causes of diseases and estimating the appearance of diseases has been increased. In the genetic diagnoses, various methods for amplifying genes, represented by a PCR (Polymerase Chain Reaction) method, are used so as to detect a gene as a target.

For detecting a gene, for example, a multichannel photodetector disclosed in JP 2002-515602 A (see pages 23 to 40 and FIGS. 1 to 9) is used. FIG. 5 is a view schematically showing a structure of a conventional multichannel photodetector. The multichannel photodetector shown in FIG. 5 amplifies a gene by controlling a temperature of a sample that is mixed with fluorochrome, subsequently irradiates the sample with light beams, and receives fluorescence excited by the irradiation, thereby conducting an analysis.

As shown in FIG. 5, the multichannel photodetector mainly is composed of a reaction unit 41, a light source unit 42 and a photoreceptive unit 43. In FIG. 5, other components except these are omitted.

In an inside of the reaction unit 41, a sample mixed with reaction reagents, fluorochrome and the like is added. In addition, the reaction unit 41 is provided with a temperature control system (not shown in the figure) for performing the above-described gene amplification.

The light source unit 42 is provided with LEDs 44a to 44d that are different in wavelength of an emitted light beam. Thus, the light source unit 42 can change the wavelength of the emitted light beam according to the fluorochrome that is mixed with the sample. In addition, the light source unit 42 is provided with filter sets 47a to 47d that transmit only light beams with certain wavelengths, and condensing lenses 46a to 46d.

Moreover, the light source unit 42 also includes dichroic mirrors 48a to 48e so that the light beams emitted by the respective LEDs (44a to 44d) may pass through a lens 49 and an output window 50 provided in a housing 45, and may enter the reaction unit 41. Furthermore, the LEDs 44a to 44d, the filter sets 47a to 47d, the condensing lenses 46a to 46d and the dichroic mirrors 48a to 48e are arranged in the housing 45 so that energy of the light beams emitted by the respective LEDs (44a to 44d) may be constant.

The photoreceptive unit 43 includes four photoreceptors 51a to 51d, because wavelengths of the excited fluorescence vary according to the kinds of fluorochrome. Moreover, the photoreceptive unit 43 is provided with filter sets 52a to 52d that transmit only light beams with certain wavelengths and lenses 53a to 53d, where filter sets 52a to 52d and lenses 53a to 53d respectively are included in the photoreceptors (51a to 51d).

Furthermore, the photoreceptive unit 43 is provided with dichroic mirrors 54a to 54e. Thus, the light beams, which are output from the reaction unit 41 and pass through an entrance window 57 provided in a housing 55 and a lens 56, pass through or are reflected by some of the dichroic mirrors and enter the corresponding photoreceptors (51a to 51d), according to the respective wavelengths of the light beams.

As mentioned above, the multichannel photodetector shown in FIG. 5 can output and receive light beams with different wavelengths, and thus can select wavelengths corresponding to the kinds of the used fluorochrome so as to detect a gene.

By the way, in genetic diagnoses, the number of diagnostic items may further increase due to the development of the genetic analytical techniques in the future, and accordingly, additional kinds of fluorochrome for being mixed with a sample may be introduced. Moreover, according to the exploitation of new kinds of fluorochrome in the future, the number of kinds of fluorochrome that can be applied to genetic diagnoses may increase. In such cases, it is required for multichannel photodetectors to have a capability of irradiating with light beams with wavelengths that correspond to the newly applied kinds of fluorochrome.

Moreover, the multichannel photodetector shown in FIG. 5 also may be utilized for fluorometry using kinds of fluorochrome other than the kinds used for detecting genes. In this case, the multichannel photodetector is required to be capable of irradiating with light beams with wavelengths that correspond to the newly applied kinds of fluorochrome.

However, the above-mentioned multichannel photodetector shown in FIG. 5 has a disadvantage that the LEDs 44a to 44d, the filter sets 47a to 47d, the condensing lenses 46a to 46d and the dichroic mirrors 48a to 48e have a complicated arrangement, in spite of having an advantage of allowing the energy of the light beams emitted by the light source unit 42 to be constant.

Therefore, there is a problem that it is structurally difficult to add LEDs to the multichannel photodetector, and accordingly, the multichannel photodetector cannot be adapted to a case where such new kinds of fluorochrome are introduced for use. This problem is also applicable to the photoreceptive unit 43.

Moreover, in the above-mentioned multichannel photodetector shown in FIG. 5, the number of dichroic mirrors necessary for outputting light beams from the light source unit 42 is larger than the number of variations of the wavelengths. Similarly, the number of dichroic mirrors necessary for leading the light beams that enter the photoreceptive unit 43 to the respective photoreceptors is also larger than the number of the variations of the wavelengths. Accordingly, the above-mentioned multichannel photodetector shown in FIG. 5 has a problem of difficulty in reducing cost.

The object of the present invention is to solve the above-mentioned problems, and to provide a light source unit in which light emitting devices can be added or removed easily, a photoreceptive unit in which photoreceptors can be added or removed easily, and a multichannel photodetector using the light source unit and the photoreceptive unit.

DISCLOSURE OF THE INVENTION

In order to attain the above-mentioned object, the light source unit according to the present invention is a light source unit, which emits a plurality of light beams with different wavelengths along the same optical path, including at least a plurality of light emitting devices and a plurality of dichroic mirrors that are different in wavelength range of a reflectible light beam, wherein the number of the plurality of dichroic mirrors is equal to the number of the plurality of light emitting devices, the plurality of light emitting devices are arranged so that output directions of the respective light emitting devices may be in parallel, the plurality of dichroic mirrors are arranged so that each of the dichroic mirrors can reflect one of emitted light beams that are emitted by the plurality of light emitting devices, and light beams reflected by the respective dichroic mirrors may pass through the same optical path in the same direction.

In the above-described light source unit according to the present invention, it is preferable that the plurality of light emitting devices are different in wavelength of an emitted light beam, and are arranged in order of wavelength of the emitted light beam.

Moreover, in order to attain the above-mentioned object, the photoreceptive unit according to the present invention is a photoreceptive unit, which receives a plurality of incident light beams with different wavelengths that enter along the same optical path, including at least a plurality of photoreceptors and a plurality of dichroic mirrors that are different in wavelength range of a reflectible light beam, wherein the number of the plurality of dichroic mirrors is equal to the number of the plurality of photoreceptors, the plurality of photoreceptors are arranged so that photoreceptive surfaces of the respective photoreceptors may be in parallel to each other, and the plurality of dichroic mirrors are arranged so that each of the incident light beams may be reflected by any one of the dichroic mirrors and may enter one of the plurality of photoreceptors, according to the wavelength of the incident light beam.

Furthermore, in order to attain the above-mentioned object, the multichannel photoredetector according to the present invention is a multichannel photodetector, including at least a reaction container, a light source unit that emits a plurality of light beams with different wavelengths along the same optical path so as to allow the plurality of light beams to enter the reaction container, and a photoreceptive unit that receives light beams output from an inside of the reaction container, wherein the light source unit includes at least a plurality of light emitting devices and a plurality of output dichroic mirrors that are different in wavelength range of a reflectible light beam, the number of the plurality of output dichroic mirrors is equal to the number of the plurality of light emitting devices, the plurality of light emitting devices are arranged so that output directions of the respective light emitting devices may be in parallel, the plurality of output dichroic mirrors are arranged so that each of the output dichroic mirrors can reflect one of light beams emitted by the plurality of light emitting devices, and light beams reflected by the respective output dichroic mirrors may pass through the same optical path in the same direction, and the photoreceptive unit includes at least a plurality of photoreceptors and a plurality of photoreceptive dichroic mirrors that are different in wavelength range of a reflectible light beam, the number of the plurality of photoreceptive dichroic mirrors is equal to the number of the plurality of photoreceptors, the plurality of photoreceptors are arranged so that photoreceptive surfaces of the respective photoreceptors may be in parallel to each other, and the plurality of photoreceptive dichroic mirrors are arranged so that each of the light beams output from the inside of the reaction container may be reflected by any one of the photoreceptive dichroic mirrors and may enter one of the plurality of photoreceptors, according to a wavelength of the light beam.

In the above-mentioned multichannel photodetector according to the present invention, it is preferable that the plurality of light emitting devices are different in wavelength of the emitted light beam, and are arranged in order of wavelength of the emitted light beam.

Moreover, in the above-mentioned multichannel photodetector according to the present invention, a mixture that contains at least a sample as a target of measurement and fluorochrome can be added in the inside of the reaction container. In this case, the light beams output from the inside of the reaction container are fluorescence of the fluorochrome excited by the light beams emitted by the light source unit.

BEST MODE FOR CARRYING OUT THE INVENTION

Embodiment 1

Figure 1:
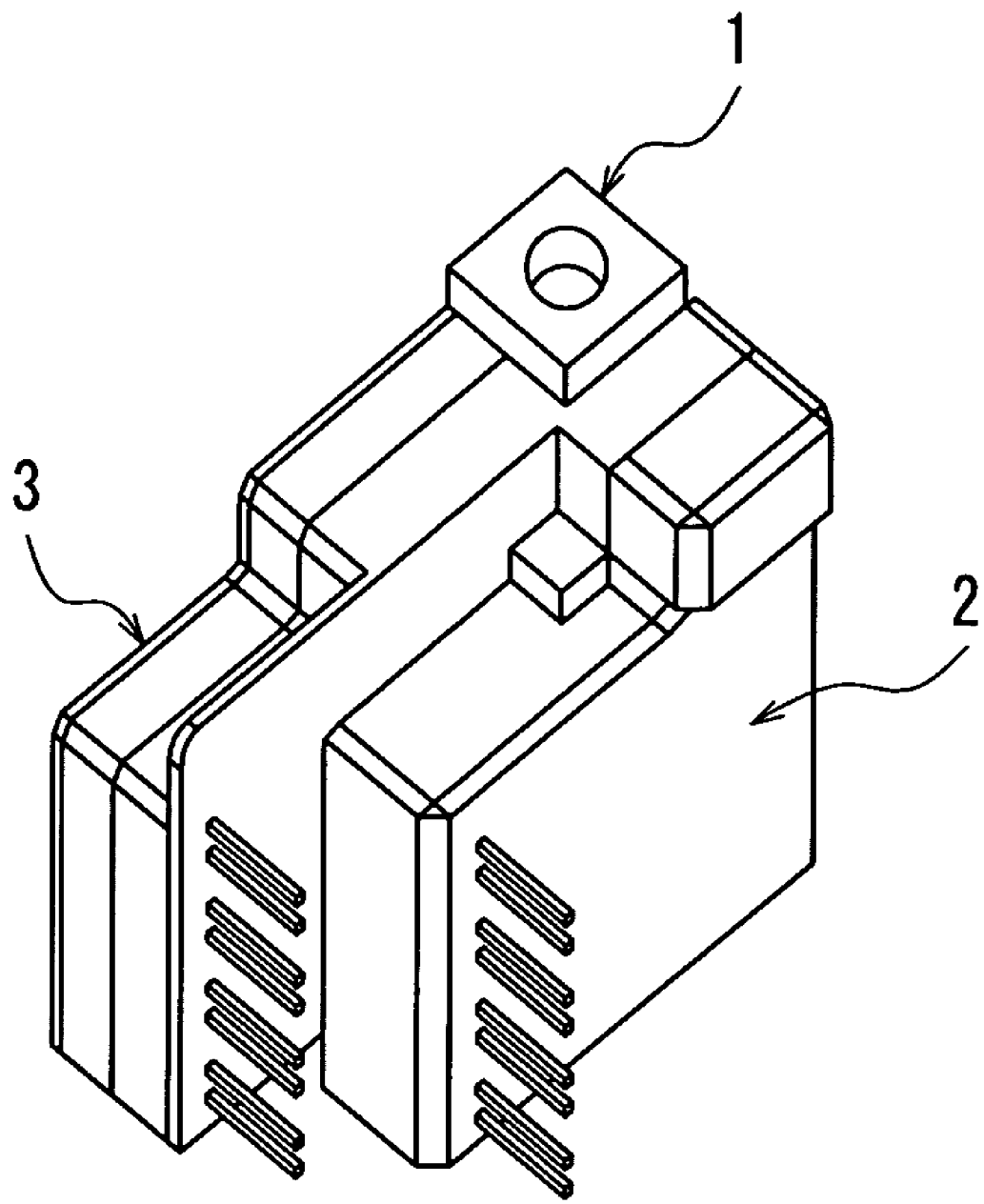
FIG. 1 is a perspective view schematically showing an outer appearance of an example of the light source unit, the photoreceptive unit and the multichannel photodetector according to the present invention.

An example of the light source unit, the photoreceptive unit and the multichannel photodetector according to the present invention will be described below with reference to FIGS. 1 to 4. FIG. 1 is a perspective view schematically showing an outer appearance of an example of the light source unit, the photoreceptive unit and the multichannel photodetector according to the present invention.

As shown in the example of FIG. 1, the multichannel photodetector includes at least a reaction container 1, a light source unit 2 and a photoreceptive unit 3. The multichannel photodetector shown in the example of FIG. 1 is an apparatus used in genetic diagnoses, being capable of irradiating with light beams a sample to which gene amplification is applied, and receiving fluorescence excited by these irradiation light beams, which will be described below. In FIG. 1, other components except these, composing the multichannel photodetector, are omitted. In addition, the multichannel photodetector shown in the example of FIG. 1 also can be utilized for fluorometry using kinds of fluorochrome other than the kinds that are applied to genetic diagnoses.

Figure 2:
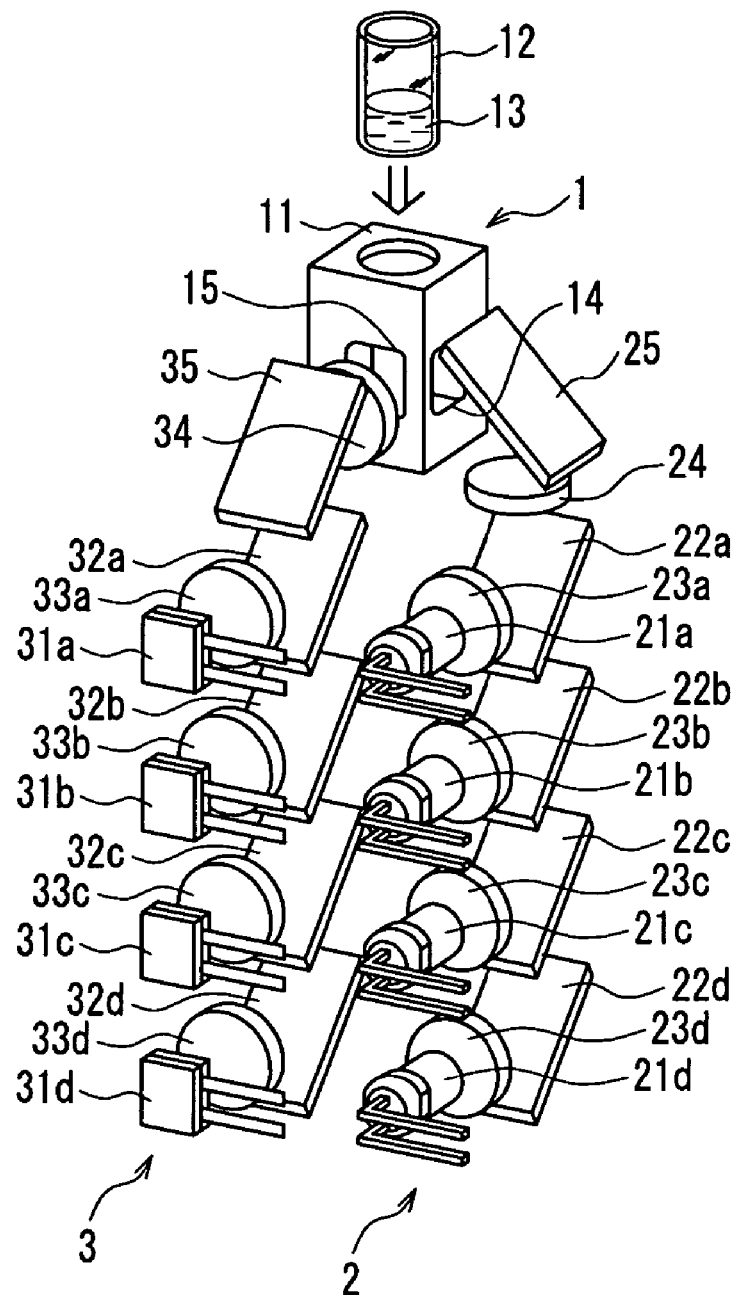
FIG. 2 is a perspective view schematically showing inner structures of the light source unit, the photoreceptive unit and the multichannel photodetector that are shown in FIG. 1.
Figure 3:
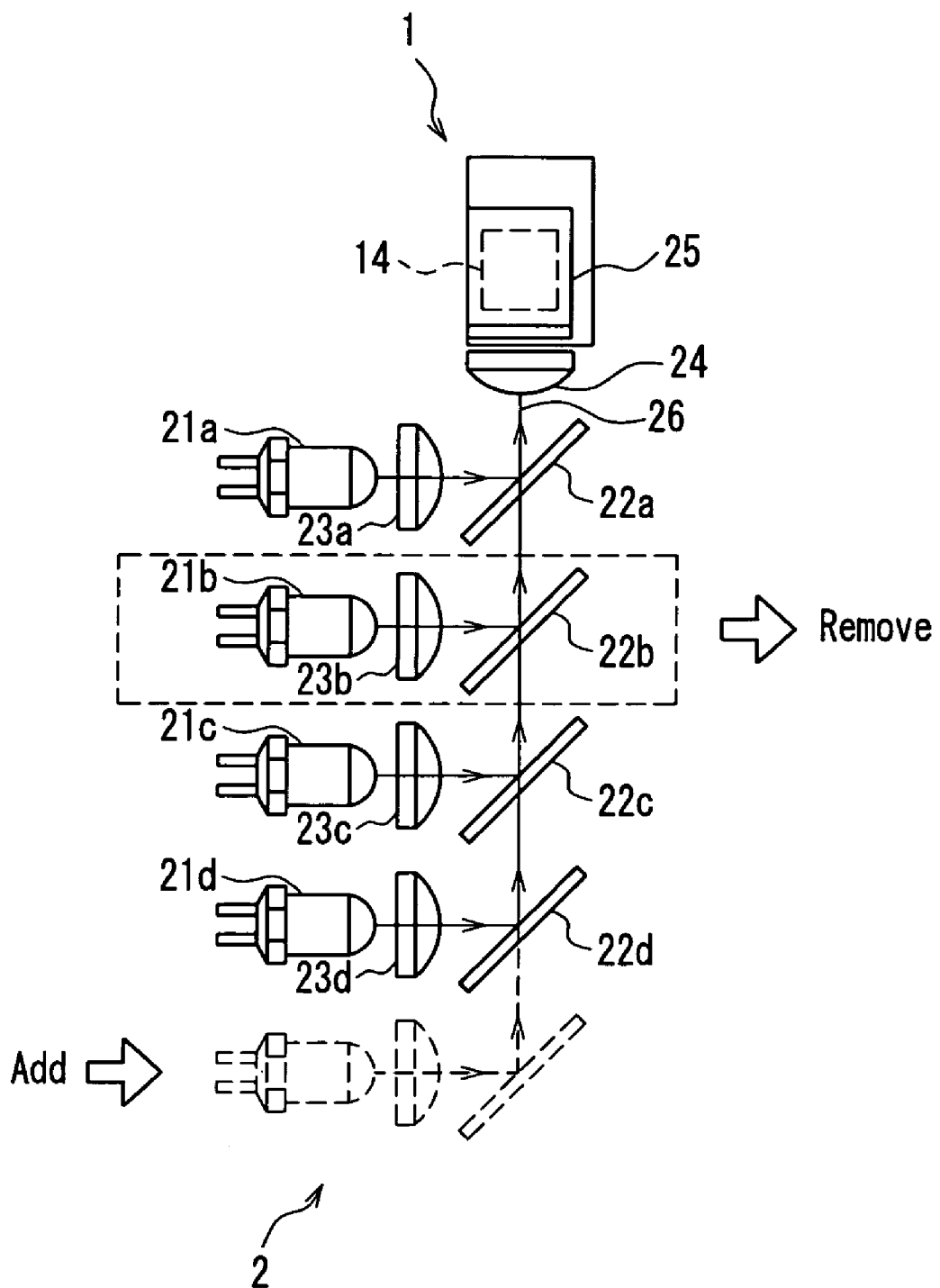
FIG. 3 is a side view showing the inner structure of the light source unit shown in FIG. 2.
Figure 4:
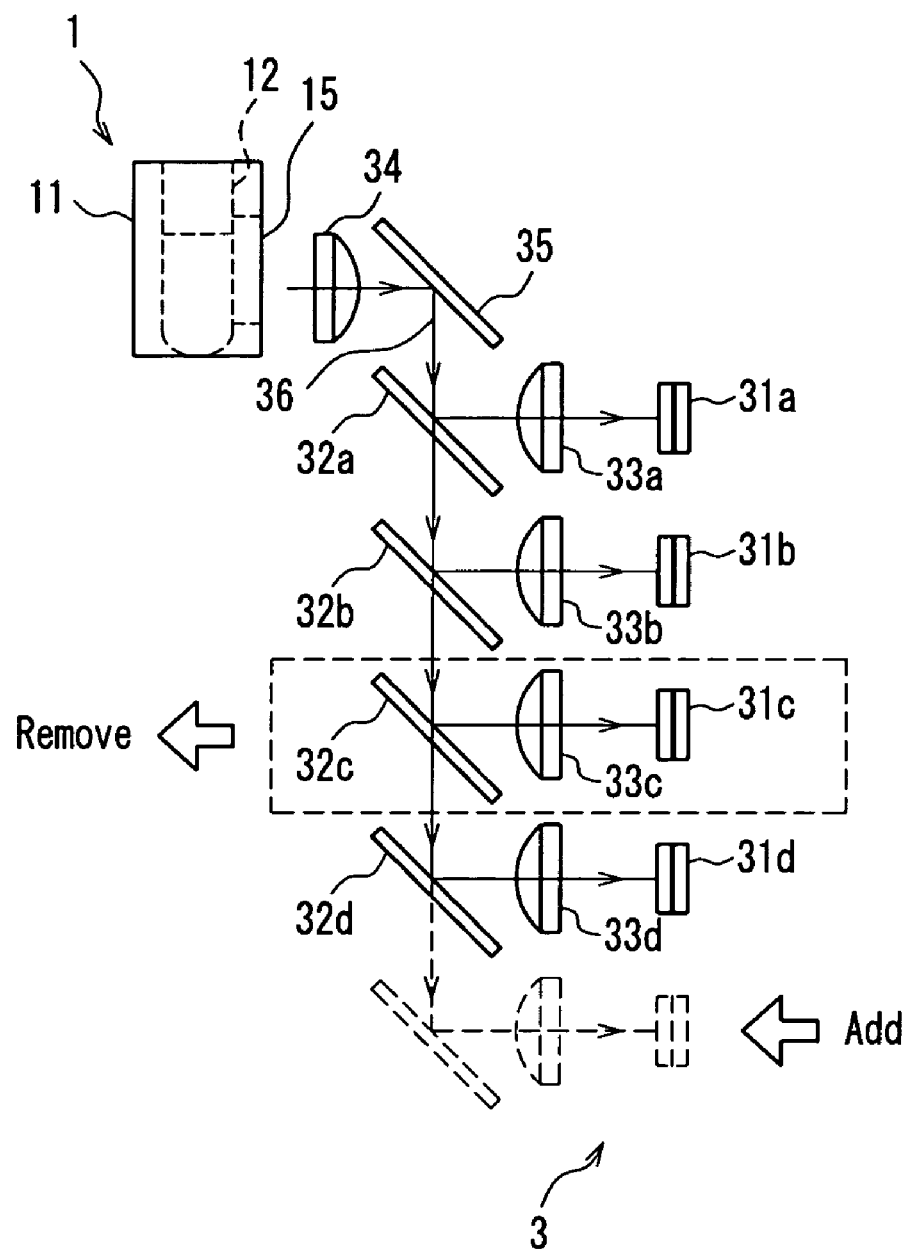
FIG. 4 is a side view showing the inner structure of the photoreceptive unit shown in FIG. 2.
Figure 5:
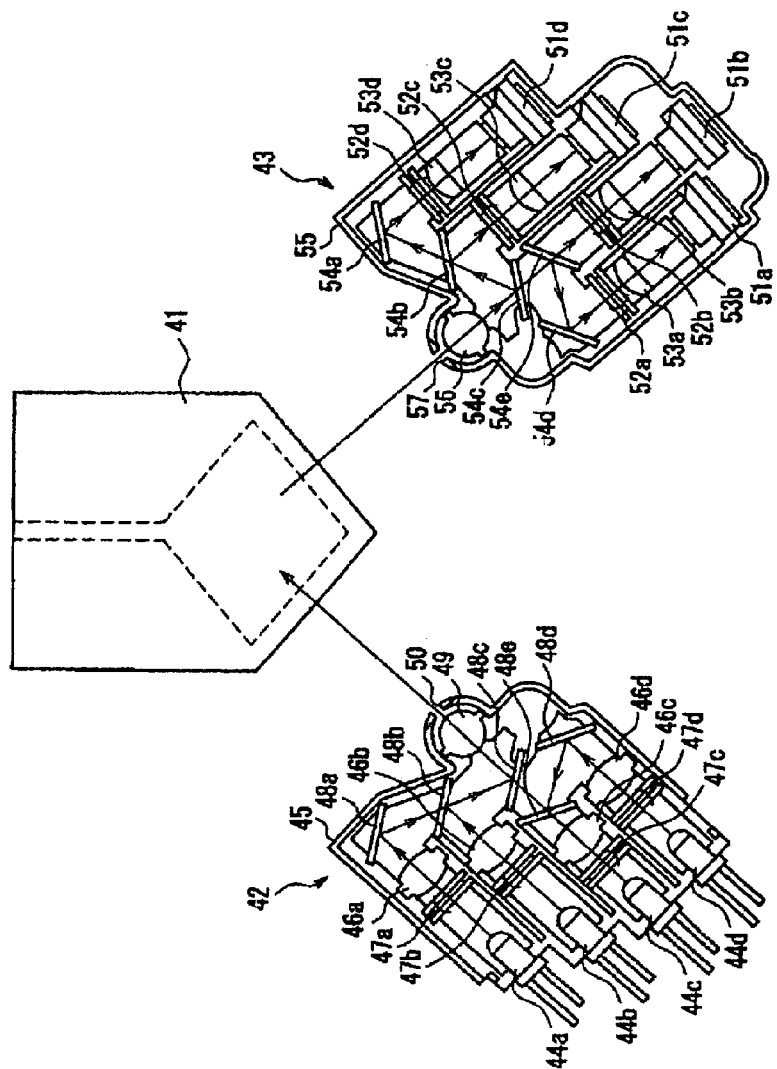
FIG. 5 is a view schematically showing a structure of a conventional multichannel photodetector.

Structures of the reaction container 1, the light source unit 2 and the photoreceptive unit 3 that compose the multichannel photodetector shown in FIG. 1 will be described below. FIG. 2 is a perspective view schematically showing inner structures of the light source unit, the photoreceptive unit and the multichannel photodetector that are shown in FIG. 1. FIG. 3 is a side view showing the inner structure of the light source unit shown in FIG. 2. FIG. 4 is a side view showing the inner structure of the photoreceptive unit shown in FIG. 2.

First, the reaction container 1 will be described. As shown in the example of FIG. 2, the reaction container 1 is composed of a transparent vessel 12 and a storage case 11 for storing the transparent vessel 12. In the example of FIG.

2, the transparent vessel 12 is shaped cylindrically, and has a part with a circular-shaped cross section. In the transparent vessel 12, a mixture 13 containing a sample as a target of a genetic diagnosis, reagents and fluorochrome and the like is added.

In addition, the storage case 11 is provided with a heating means such as a heater for performing gene amplification that is represented by, for example, a PCR method, which is not shown in the figure, though. Thus, when genes are amplified by being subjected to the gene amplification, the fluorochrome is excited by light beams that are emitted by the light source unit 2 to the reaction container 1, and light beams are output from an inside of the reaction container 1. The thus output light beams are received by the photoreceptive unit 3.

Moreover, the storage case 11 (the reaction container 1) is provided with an entrance window 14 for allowing the light beams emitted by the light source unit 2 to enter an inside of the transparent vessel 12, and an output window 15 for releasing the light beams that are output from the inside of the transparent vessel 12 toward the outside. Here, positions of the entrance window 14 and the output window 15 are not particularly limited, and the entrance window 14 and the output window 15 may be provided on either an upper face, a bottom face or side faces of the storage case 11.

However, when the transparent vessel 12 has a part with a circular-shaped cross section, the entrance window 14 and the output window 15 preferably are provided in positions (on the side faces) facing to the part with the circular-shaped cross section. This is because, light beams are repeatedly reflected by an inner face of the transparent vessel 12 in the part with the circular-shaped cross section, and therefore, according to such an embodiment, the light beams with high energy can be led to the photoreceptive unit 3.

In addition, a shape of the transparent vessel 12 is not particularly limited, but if light beams enter a part of a side face of the transparent vessel 12, and light beams are obtained from another part of the side face of the transparent vessel 12 as shown in FIG. 2, a shape of the transparent vessel 12 having a part with a circular-shaped cross section, for example, a cylindrical shape is preferable, as mentioned above. Furthermore, in the present invention, a structure of the reaction container 1 is not particularly limited. For example, a shade film may be provided in region other than regions of the entrance window 14 and the output window 15 on a surface of the transparent vessel 12.

Next, the light source unit 2 will be described. As shown in the example of FIGS. 2 and 3, the light source unit 2 includes at least light emitting devices 21a to 21d and the equal number of output dichroic mirrors 22a to 22d.

In the example of FIGS. 2 and 3, the light emitting devices 21a to 21d are different in wavelength of an emitted light beam, and are arranged in order of wavelength of the emitted light beam so that output directions of the respective light emitting devices may be in parallel. Specifically, the wavelengths of the light beams emitted by the respective light emitting devices 21a, 21b, 21c and 21d increase in this order.

Moreover, in the example of FIGS. 2 and 3, the output dichroic mirrors 22a to 22d have characteristics of reflecting only light beams with certain wavelengths or shorter (high-pass characteristics), and are different in the wavelength range of a reflectible light beam. Maximum wavelengths of the reflectible light beams of the respective output dichroic mirrors 22a, 22b, 22c and 22d increase in this order.

Furthermore, the output dichroic mirrors 22a to 22d are arranged so that each of them can reflect one of the light beams emitted by the plurality of light emitting devices, and the reflected light beams by the respective output dichroic mirrors may pass through the same optical path 26 in the same direction. In the example of FIGS. 2 and 3, the output dichroic mirrors 22a to 22d are disposed along an arrangement of the light emitting devices 21a to 21d in parallel so that reflection surfaces may be in parallel to each other.

In FIGS. 2 and 3, reference numerals 23a to 23d denote lenses for condensing the light beams emitted by the light emitting devices 21a to 21d. Reference numeral 24 denotes a lens for condensing the light beams reflected by the output dichroic mirrors 22a to 22d. Reference numeral 25 is a total reflection mirror for leading the light beams reflected by the output dichroic mirrors 22a to 22d to the output window 15 of the reaction container 1.

According to the above-mentioned structure, the light source unit 2 can emit a plurality of light beams with different wavelengths along the same optical path so as to allow the light beams to enter the reaction container 1. In addition, according to the light source unit 2, an arrangement of the light emitting devices and the dichroic mirrors may be simplified more, compared with the light source unit used in the conventional multichannel photodetector. Therefore, as shown in FIG. 3, the light emitting devices may be added or removed easily, according to the kinds of fluorochrome to be used. Furthermore, since the number of the light emitting devices and the number of the output dichroic mirrors can be equal, the light source unit 2 of the present invention can reduce the cost more, compared with the conventional light source unit.

Moreover, in the example shown in FIGS. 2 and 3, the light emitting devices are arranged so that the light emitting device which is shorter in wavelength of the emitted light beam may be closer to the reaction container 1, and an optical path of the emitted light beam with a shorter wavelength has a shorter length. Therefore, by using the light source unit 2, energy of the light beams entering the reaction container 1 may be substantially constant, regardless of the wavelengths of the light beams.

In the light source unit according to the present invention, the number of the light emitting devices is not limited to the above-mentioned example. The number of the light emitting devices may be determined according to the number of the kinds of fluorochrome to be used in a genetic diagnosis. For example, in the case where five kinds of fluorochrome are used in a genetic diagnosis, and these kinds of fluorochrome have different excitation peak wavelengths, the number of the light emitting devices is five. Even in the case where the five kinds of fluorochrome are used in a genetic diagnosis, but if they are not used at the same time, alternatively, some of the excitation peak wavelengths thereof are equal, and the number of the light emitting devices may be five or smaller. Here, the number of the output dichroic mirrors is equal to the number of the light emitting devices.

Moreover, in the light source unit according to the present invention, the wavelengths of the light beams emitted by the light emitting devices are determined according to excitation peak wavelengths of general kinds of fluorochrome that are used for fluorometry. Therefore, the light emitting devices are selected according to the required wavelengths. For example, in the case where the kinds of fluorochrome listed below in Table 1 are used in a genetic diagnosis, light emitting diodes or semiconductor lasers that emit light beams with the wavelengths listed below in Table 2 are used as the light emitting devices 21a to 21d.

In the present invention, the light emitting devices are not limited to the above-described light emitting diodes and semiconductor lasers. Light emitting devices other than these, for example, xenon lamps or halogen lamps, may be used. Moreover, the wavelengths of the light beams emitted by the respective light emitting devices may be equal.

TABLE 1

| | name of fluorochrome | | | |
|---|---|---|---|---|
| | FAM | JOE | TAMRA | ROX |
| excitation peak wavelength (nm) | 470 | 500 | 530 | 560 |
| fluorescent peak wavelength (nm) | 520 | 550 | 580 | 610 |

TABLE 2

| | light emitting device | | | |
|---|---|---|---|---|
| | 21a | 21b | 21c | 21d |
| wavelength (nm) | 470 | 500 | 530 | 560 |

In the case of using the light emitting devices that emit light beams with the wavelengths listed above in Table 2, dichroic mirrors that reflect light beams with the wavelength ranges listed below in Table 3 are used as the output dichroic mirrors 22a to 22d shown in FIGS. 2 and 3.

TABLE 3

| | output dichroic mirror | | | |
|---|---|---|---|---|
| | 22a | 22b | 22c | 22d |
| reflective range | 485 nm or shorter | 515 nm or shorter | 545 nm or shorter | 575 nm or shorter |

In addition, the light source unit according to the present invention may be provided with an actinometer for monitoring light amounts of the emitted light beams. In this case, since deterioration of the light emitting devices and influences of change in a surrounding temperature upon the light emitting devices also can be monitored from measurement of the actinometer, the accuracy of the genetic diagnosis can be enhanced. Moreover, a position for providing the actinometer may be within the optical path between the output dichroic mirror 22a and the reaction container 1 in the example of FIGS. 2 and 3, and is not limited particularly.

Next, the photoreceptive unit 3 according to the present invention will be described. As shown in the example of FIGS. 2 and 4, the photoreceptive unit 3 according to the present invention includes at least photoreceptors 31a to 31d and the equal number of photoreceptive dichroic mirrors 32a to 32d. The photoreceptors 31a to 31d are arranged so that photoreceptive surfaces of the respective photoreceptors may be in parallel.

The photoreceptive dichroic mirrors 32a to 32d have characteristics of reflecting light beams with certain wavelengths or longer (low-pass characteristics), and are different in wavelength range of a reflectible light beam. In the example shown in FIGS. 2 and 4, the minimum wavelengths of reflectible light beams of the respective photoreceptive dichroic mirrors 32a, 32b, 32c and 32d decrease in this order.

In addition, the photoreceptive dichroic mirrors 32a to 32d are arranged so that each of the light beams output from the inside of the reaction container 1 may be reflected by any one of the photoreceptive dichroic mirrors and may enter one of the photoreceptors 31a to 31d, according to the wavelength of the light beam. In the example of FIGS. 2 and 4, the photoreceptive dichroic mirrors 32a to 32d are disposed along an arrangement of the photoreceptors 31a to 31d in parallel so that the reflection surfaces may be in parallel to each other.

In FIGS. 2 and 4, reference numerals 33a to 33d denote lenses for condensing the light beams reflected by the photoreceptive dichroic mirrors 32a to 32d. Reference numeral 34 denotes a lens for condensing the light beams output from the inside of the reaction container 1 via the output window 15. Reference numeral 35 is a total reflection mirror for leading the light beams output from the inside of the reaction container to the photoreceptive unit.

According to the above-mentioned structure, the photoreceptive unit 3 of the present invention can receive a plurality of incident light beams with different wavelengths that enter along the same optical path. In addition, according to the photoreceptive unit 3 of the present invention, an arrangement of the photoreceptors and the dichroic mirrors may be simplified more, compared with the photoreceptive unit used for the conventional multichannel photodetector. Therefore, as shown in FIG. 4, the photoreceptors may be added or removed easily, according to the kinds of fluorochrome to be used. Furthermore, since the number of the photoreceptors and the number of the photoreceptive dichroic mirrors may be equal, the photoreceptive unit 3 of the present invention can reduce the cost more, compared with the photoreceptive unit used for the conventional multichannel photodetector.

Moreover, in the example shown in FIGS. 2 and 4, the photoreceptive dichroic mirrors are arranged so that the photoreceptive dichroic mirror that is longer in minimum wavelength of a reflectible light beam may be closer to the reaction container 1, and an optical path of the incident light beam with a shorter wavelength has a longer length.

In the photoreceptive unit according to the present invention, the number of the photoreceptors and the photoreceptive dichroic mirrors are not limited to the above-mentioned example. Similarly to the number of the light emitting devices, the number of the photoreceptors and the photoreceptive dichroic mirrors may be determined according to the number of the general kinds of fluorochrome that are used for fluorometry.

Moreover, in the photoreceptive unit of the present invention, wavelength ranges of the reflectible light beams of the photoreceptive dichroic mirrors are set according to the kinds of fluorochrome to be used in a genetic diagnosis. For example, in the case of using the kinds of fluorochrome listed above in Table 1 in a genetic diagnosis, dichroic mirrors that reflect light beams with the wavelength ranges listed below in Table 4 are used as the photoreceptive dichroic mirrors 32a to 32d shown in FIGS. 2 and 4.

TABLE 4

| | photoreceptive dichroic mirror | | | |
|---|---|---|---|---|
| | 32a | 32b | 32c | 32d |
| reflection range | 605 nm or longer | 575 nm or longer | 545 nm or longer | 515 nm or longer |

In addition, similarly to the light source unit, the photoreceptive unit according to the present invention also may be provided with an actinometer for monitoring light amounts of the incident light beams. In this case, since disorder in the reactive container (for example, incorporation of foreign substances into the inside of the reaction container) can be monitored from measurement of the actinometer, the accuracy of the genetic diagnosis can be enhanced. Moreover, a position for providing the actinometer may be within the optical path between the photoreceptive dichroic mirror 32a and the reaction container 1 in the example of FIGS. 2 and 4, and is not limited particularly.

As mentioned above, according to the multichannel photodetector of the present invention, while the performance is secured to be equivalent to the conventional one, the inner structures of the light source unit and the photoreceptive unit can be simplified more than those of the conventional multichannel photodetector. Therefore, the multichannel photodetector of the present invention easily can be adapted to the case of increasing the number of the kinds of fluorochrome to be used.

In the above-mentioned example, the case of using the light source unit, the photoreceptive unit and the multichannel photodetector according to the present invention in a genetic diagnosis is described, however, the present invention is not limited to this example. For example, the light source unit, the photoreceptive unit and the multichannel photodetector according to the present invention also can be applied to immune reaction measurement and conventional spectrophotometry.

INDUSTRIAL APPLICABILITY

As mentioned above, according to the light source unit of the present invention, the light emitting devices can be added or removed easily, and according to the photoreceptive unit of the present invention, the photoreceptors can be added or removed easily. Therefore, the multichannel photodetector according to the present invention can be applied to the cases where the number of diagnostic items are increased due to the development of the genetic analytical techniques, and new kinds of fluorochrome are exploited. In addition, the number of members included in the multichannel photodetector of the present invention can be smaller than that of the conventional multichannel photodetector, thereby leading to the cost reduction.

The invention claimed is:

1. A multichannel photodetector, comprising at least a reaction container, a light source unit that emits a plurality of light beams with different wavelengths along a same optical path so as to allow the plurality of light beams to enter the reaction container, and a photoreceptive unit that receives light beams output from an inside of the reaction container, wherein the light source unit comprises at least a plurality of light emitting devices and a plurality of output dichroic mirrors that are different in wavelength range of a reflectible light beam and an actinometer for monitoring light amounts of the emitted light beams, the number of the plurality of output dichroic minors is equal to the number of the plurality of light emitting devices, the plurality of light emitting devices are arranged so that output directions of the respective light emitting devices are in parallel, the plurality of output dichroic mirrors are arranged so that each of the output dichroic minors reflects one of light beams emitted by the plurality of light emitting devices, and light beams reflected by the respective output dichroic mirrors pass through the same optical path in the same direction, the actinometer being disposed between the reaction container and the output dichroic mirror positioned nearest the reaction container, and the photoreceptive unit comprises at least a plurality of photoreceptors and a plurality of photoreceptive dichroic mirrors that are different in wavelength range of a reflectible light beam, the number of the plurality of photoreceptive dichroic mirrors is equal to the number of the plurality of photoreceptors, the plurality of photoreceptors are arranged so that photoreceptive surfaces of the respective photoreceptors are parallel to each other, and the plurality of photoreceptive dichroic mirrors are arranged so that each of the light beams output from the inside of the reaction container is reflected by any one of the photoreceptive dichroic mirrors and enters one of the plurality of photoreceptors, according to a wavelength of the light beam.

2. The multichannel photodetector according to claim 1, wherein the plurality of light emitting devices are different in wavelength of the emitted light beam, and are arranged in order of wavelength of the emitted light beam.

3. The multichannel photodetector according to claim 1, wherein a mixture that contains at least a sample as a target of measurement and fluorochrome is added in the inside of the reaction container, and the light beams output from the inside of the reaction container are fluorescence of the fluorochrome excited by the light beams emitted by the light source unit.

* * * * *